US009724688B2

(12) United States Patent
Kobayashi et al.

(10) Patent No.: US 9,724,688 B2
(45) Date of Patent: Aug. 8, 2017

(54) ISOLATOR SYSTEM (71) Applicant: Panasonic Healthcare Holdings Co., Ltd., Tokyo (JP)

(72) Inventors: Koichi Kobayashi, Tochigi (JP); Yasuhiko Yokoi, Hyogo (JP); Hironobu Sekine, Gunma (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 0 days.

(21) Appl. No.: 15/055,169

(22) Filed: Feb. 26, 2016

(65) Prior Publication Data
US 2016/0175833 A1 Jun. 23, 2016

Related U.S. Application Data (63) Continuation of application No. PCT/JP2014/075586, filed on Sep. 26, 2014.

(30) Foreign Application Priority Data

Sep. 30, 2013 (JP) .................................. 2013-203337

(51) Int. Cl.
*B01J 19/00* (2006.01)
*B01L 1/02* (2006.01)
(Continued)

(52) U.S. Cl.
CPC ................. *B01L 1/025* (2013.01); *B01L 1/04* (2013.01); *B25J 21/02* (2013.01); *C12M 37/00* (2013.01);
(Continued)

(58) Field of Classification Search
CPC . C12M 37/00; C12Q 1/24; G01N 1/31; B01L 1/04; F24F 3/16
(Continued)

(56) References Cited

U.S. PATENT DOCUMENTS

2003/0197450 A1 10/2003 Ross
2011/0212513 A1 9/2011 Yokoi et al.

FOREIGN PATENT DOCUMENTS

EP 2492025 A1 8/2012
JP 2005-235882 A 9/2005
(Continued)

OTHER PUBLICATIONS

International Search Report dated Jan. 6, 2015, issued in corresponding International Application No. PCT/JP2014/075586. (w/ partial English translation).
(Continued)

*Primary Examiner* — Monzer R Chorbaji
(74) *Attorney, Agent, or Firm* — McDermott Will & Emery LLP (57) ABSTRACT

An isolator system including: a box-shaped body case having, in an interior thereof, a work space for operation in a sterile environment and also having, in a front surface thereof, an insertion portion into which a worker's arm is inserted; and an air-conditioning portion configured to supply gas in the work space of the body case or to discharge gas in the work space, a bottom of the work space being configured with a work plate, a discharge path configured to discharge gas in the work space being formed below the work plate, the work plate being configured with first and second work plates obtained by dividing the work plate into right and left parts, a receiving portion being located below the first work plate, the receiving portion being arranged extending towards the second work plate on a side edge of the first work plate, the side edge of the first work plate being in contact with the second work plate, a side edge of the second work plate for being in contact with the first work plate being placed detachably on the receiving portion.

8 Claims, 8 Drawing Sheets

(51) Int. Cl.
 *B25J 21/02* (2006.01)
 *C12M 1/12* (2006.01)
 *B01L 1/04* (2006.01)
(52) U.S. Cl.
 CPC ... *B01L 2200/028* (2013.01); *B01L 2200/087* (2013.01); *B01L 2200/141* (2013.01); *B01L 2300/1894* (2013.01)
(58) Field of Classification Search
 USPC ...................................................... 422/500
 See application file for complete search history.

(56) References Cited

FOREIGN PATENT DOCUMENTS

| JP | 2007-105597 A | 4/2007 | | |
|---|---|---|---|---|
| JP | 2011-177091 A | 9/2011 | | |
| WO | 88/07574 A1 | 10/1988 | | |
| WO | WO 88/07574 | * | 10/1988 | ............. C12M 1/00 |
| WO | 2013/125374 A1 | 8/2013 | | |

OTHER PUBLICATIONS

Extended European Search Report issued in corresponding European Patent Application No. 14849112.9, mailed on Jun. 24, 2016.

* cited by examiner

ISOLATOR SYSTEM

CROSS-REFERENCE TO RELATED APPLICATIONS

This is a continuation application of International Patent Application No. PCT/JP2014/075586 filed Sep. 26, 2014, which claims the benefit of priority to Japanese Patent Application No. 2013-203337 filed Sep. 30, 2013. The full contents of the International Patent Application are incorporated herein by reference.

BACKGROUND

Technical Field

The present disclosure relates to an isolator system used for a regenerative medical experiment environmental device and a pharmaceutical experiment environmental device, in which a work hand is inserted into a box shaped work space to conduct work.

Description of the Related Art

Japanese Patent Application Laid-open Publication No. 2011-177091 discloses an isolator in which the bottom of its working chamber is configured with a working plate and which includes a discharge path below the working plate and a centrifugal machine below the middle of the working plate. In the isolator, its working chamber is separated into an operation area and an auxiliary working area. The working plate of the isolator has a recess for housing a door, and a door of a joint box to which an incubator is mounted is housed in the recess so as to be a part of the working plate.

The present disclosure is to provide an isolator system whose ease of cleaning and workability are improved.

SUMMARY

An isolator system according to an aspect of the present invention, includes: a box-shaped body case having, in an interior thereof, a work space for operation in a sterile environment and also having, in a front surface thereof, an insertion portion into which a worker's arm is inserted; and an air-conditioning portion configured to supply gas in the work space of the body case or to discharge gas in the work space, a bottom of the work space being configured with a work plate, a discharge path configured to discharge gas in the work space being formed below the work plate, the work plate being configured with first and second work plates obtained by dividing the work plate into right and left parts, a receiving portion being located below the first work plate, the receiving portion being arranged extending towards the second work plate on a side edge of the first work plate, the side edge of the first work plate being in contact with the second work plate, a side edge of the second work plate for being in contact with the first work plate being placed detachably on the receiving portion.

Other features of the present invention will become apparent from descriptions of the present specification and of the accompanying drawings.

BRIEF DESCRIPTION OF THE DRAWINGS

For more thorough understanding of the present invention and advantages thereof, the following description should be read in conjunction with the accompanying drawings, in which.

DETAILED DESCRIPTION

At least the following details will become apparent from descriptions of the present specification and of the accompanying drawings.

Hereinafter, embodiments will be described in detail with reference to drawings as necessary. However, a description in more detailed than necessary may be omitted. For example, detailed descriptions of well-known matters and the repeated descriptions of substantially the same configurations may be omitted. This is to prevent the following description from being unnecessarily redundant than necessary, and to facilitate the understanding of a person skilled in the art.

Note that the inventors provide the accompanying drawings and the following descriptions to help a person skilled in the art fully understand the present disclosure, and are not intended to limit the subject matters described in the claims thereby.

Embodiment 1

An isolator system 100 will be described hereinafter as an example of an isolator system in an embodiment 1 with reference to FIGS. 1 to 8.

The isolator system 100 in the embodiment 1 is a device configured to perform, for example, work for cell culture, manipulation, observation, etc., in a sterilized environment. Note that sterilization means an act of killing microorganisms, cells and the like, to bring a state closer to a sterile environment.

Note that, in the present embodiment, it is assumed that the Z axis is an axis along a vertical direction in which the isolator system 100 is provided in a standing manner, and a direction toward the upper side is +Z direction and a direction toward the lower side (downward) is −Z direction. It is assumed that the Y axis is an axis along a direction perpendicular to the front surface and the back surface of the isolator system 100, and a direction from the front surface, where openings for conducting work in the interior of a work space are provided, toward the back surface opposite to the front surface is −Y direction, and a direction from the back surface toward the front surface is +Y direction. It is assumed that the X axis is an axis along a direction perpendicular to the left and right side surfaces when seen from the front, and a direction from the left side surface toward the right side surface when seen from the front is +X direction, and a direction from the right side surface toward the left side surface is −X direction.

[1. Isolator System]

Figure 1:
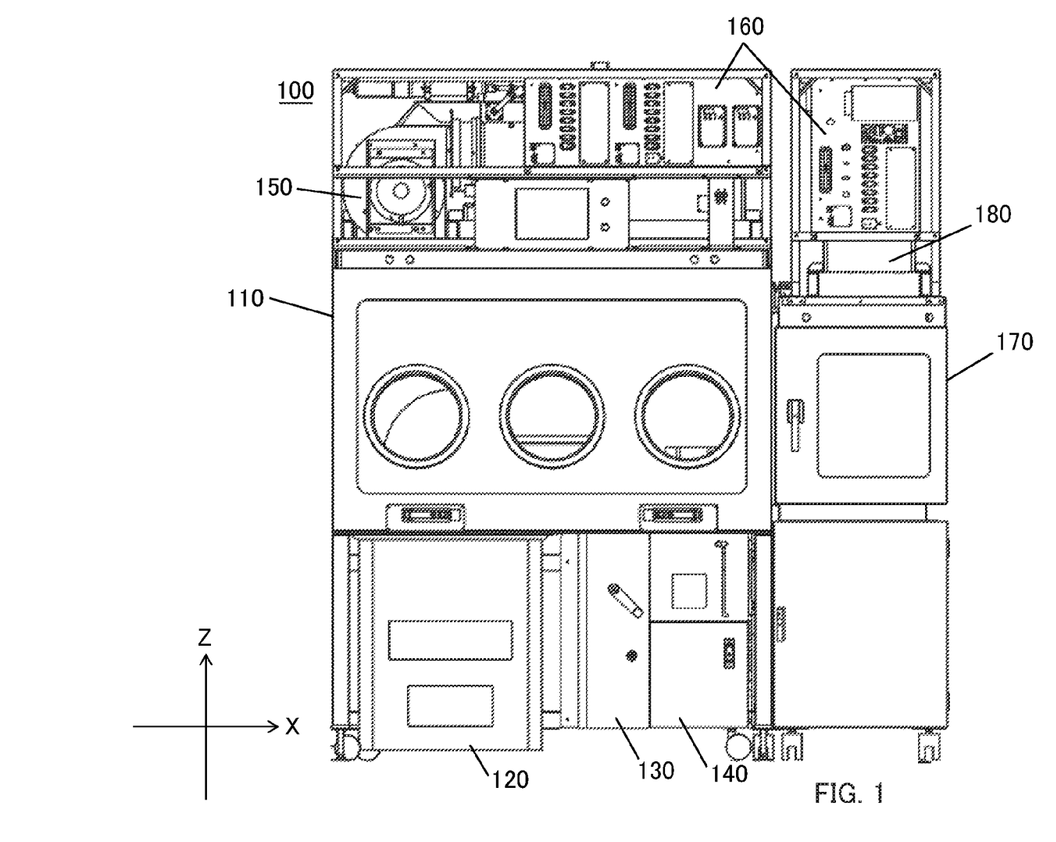
FIG. 1 is a front view of an isolator system according to the embodiment 1.
Figure 2:
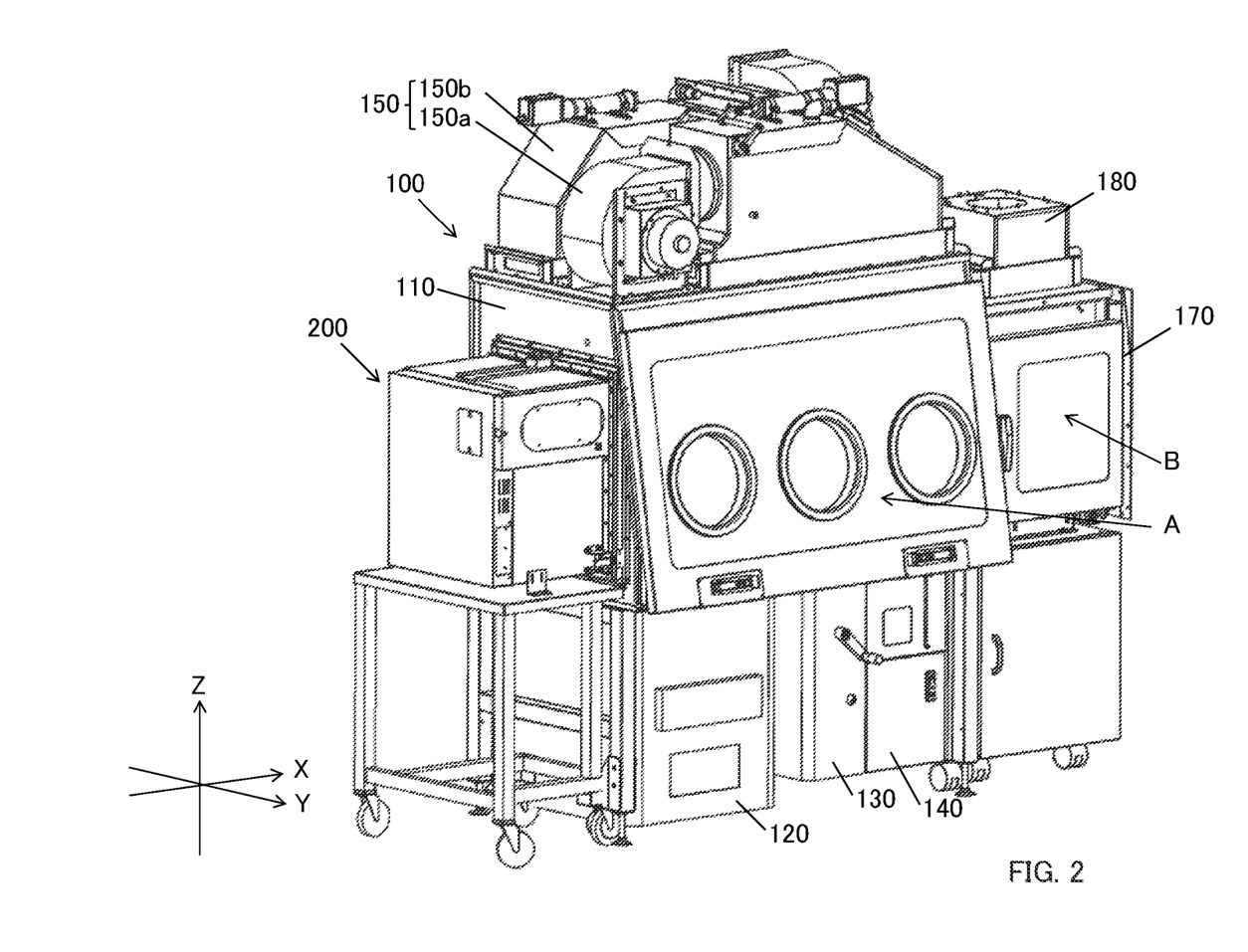
FIG. 2 is a perspective view of the isolator system when incubator according to the embodiment 1 is mounted thereon.
Figure 3:
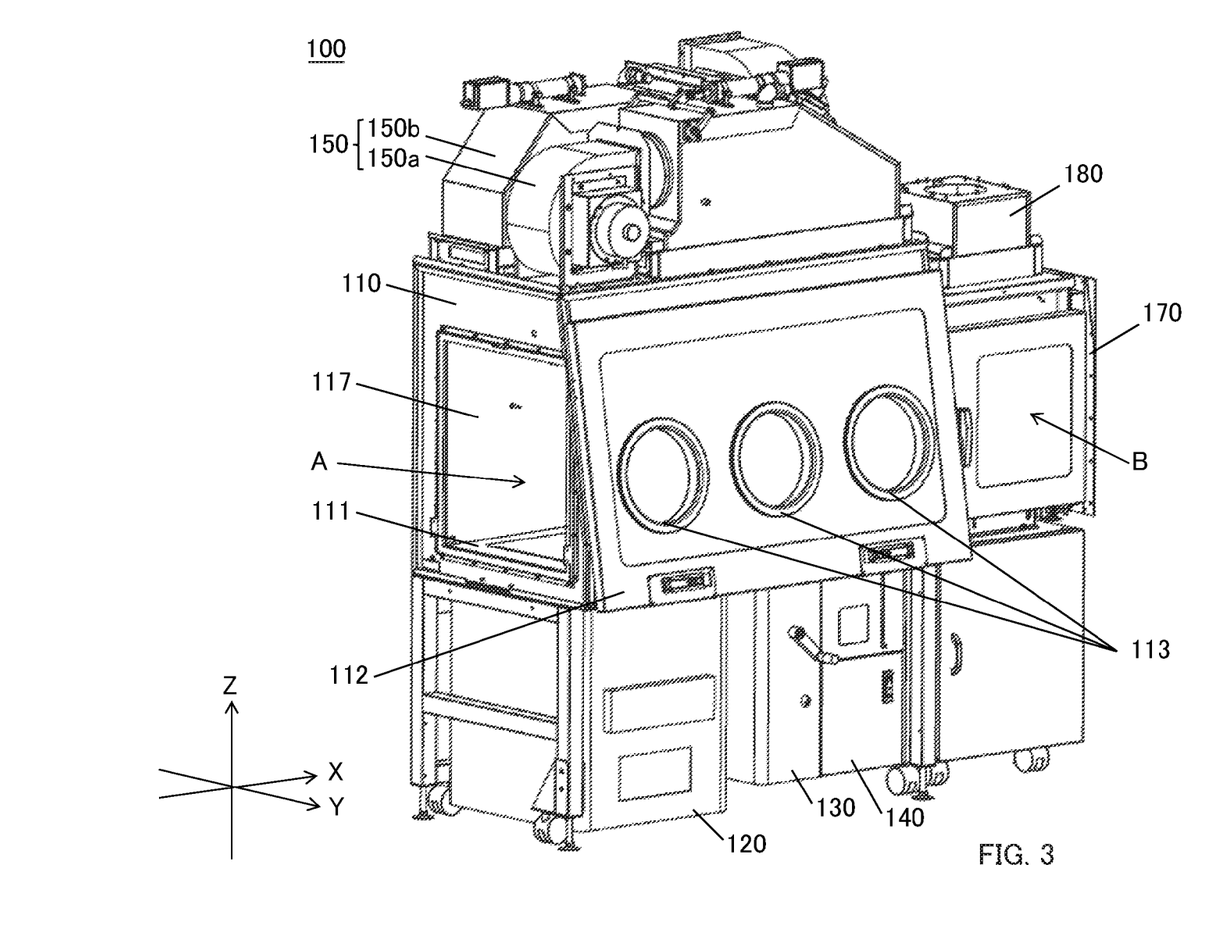
FIG. 3 is a perspective view of the isolator system according to the embodiment 1.

A configuration of the isolator system 100 will be described with reference to FIGS. 1 to 3. FIGS. 1 and 2 are respectively a front view and a perspective view illustrating the isolator system 100 according to the embodiment 1. FIG. 3 is a perspective view of the isolator system 100 when an incubator 200 is mounted thereon, according to the embodiment 1.

As illustrated in FIG. 1, the isolator system 100 according to the embodiment 1 includes: a glove box 110; a centrifuge unit 120; an observation unit 130; a sterilization unit 140; an air-conditioning unit 150; a control unit 160; a pass box 170; and an air-conditioning unit 180.

As illustrated in FIG. 2, the glove box 110 includes a substantially box-shaped work space A, formed in the interior thereof, that is isolated from the surroundings to conduct work in the sterilized environment. The detailed configuration will be described later. The centrifuge unit 120 is provided below the glove box 110, and can be connected from the work space A. The centrifuge unit 120 includes, in the interior thereof, a centrifuge configured to centrifuge a sample to work with in the work space A. The observation unit 130 is provided below the glove box 110, and can be connected from the work space A. The observation unit 130 includes, in the interior thereof, an observation device configured to observe a sample to work with in the work space A. Further, the observation unit 130 includes: a lifting mechanism capable of lifting and lowering the observation device provided in the interior thereof; and a handle, provided in the exterior, with which the lifting mechanism is operated. A worker operates the lifting mechanism using the handle, so that the observation device can be moved up into the work space A when the observation device is used and the observation device can be housed in the observation unit 130 when the observation unit 130 is not used. The sterilization unit 140 is provided below the glove box 110, to supply a sterilizing substance such as hydrogen peroxide into the glove box 110. The sterilization unit 140 in the present embodiment is configured to spray sterilizing mist, obtained by converting sterilizing liquid into mist, through a nozzle provided in the glove box 110, to sterilize the interior thereof.

The air-conditioning unit 150 is provided above the glove box 110, and is configured to control the air conditioning in the interior thereof. The air-conditioning unit 150 includes a supply unit 150a and a discharge unit 150b. The air-conditioning unit 150 includes an inlet and an outlet in the top plate in the glove box 110. The outside air is supplied from the inlet into the work space A, and the gas in the work space A is discharged from the outlet. In the glove box 110, a particulate trap filter such as an HEPA filter is mounted to the inlet to secure the sterile environment in the interior, and the air is supplied through the particulate trap filter into the glove box 110. Further, the HEPA filter is mounted to the outlet, and the gas in the glove box 110 is discharged from the interior of the glove box 110 through the HEPA filter.

The control unit 160 is provided above the glove box 110 and the pass box 170, and is configured to control the operations of the devices such as the sterilization unit 140 and the air-conditioning units 150 and 180.

The pass box 170 is provided on a side surface of the glove box 110, in order for a worker to enter a workpiece from the exterior into the interior of the work space A. In the interior of the pass box 170, a conveyance space B to temporarily store a workpiece is formed. The conveyance space B is separated from its environment and has air tightness. A workpiece is sterilized in the conveyance space B before the workpiece is entered into the work space A from the exterior. On a side surface of the pass box 170, an opening for conveying a workpiece is provided. The glove box 110 and the pass box 170 are fixed facing the opening provided on the side surface of the glove box 110. Thus, the work space A and the conveyance space B communicates with each other while maintaining air tightness. A door which is capable of opening/closing is attached to the opening of the pass box 170. The door can separate the conveyance space B from the work space A while maintaining air tightness. The air-conditioning unit 180 is provided above the pass box 170, and controls the air conditioning in the interior of the conveyance space B.

In the isolator system 100, the incubator 200 is mounted on the opposite side surface to the side surface to which the pass box 170 is provided in the glove box 110. The incubator 200 includes a storage chamber (not shown) in the interior thereof. The storage chamber is a chamber for storing a culture. And the storage chamber is, for example, a rectangular parallelepiped-shaped box body, and is partitioned as a space to restrain bacterial invasion from the exterior. The storage chamber is partitioned with, for example, stainless steel plates. The incubator 200 is demountably configured with respect to the isolator system 100. Thus, culture can be controlled in each incubator 200. For example, a dedicated incubator 200 can be used for each donor, thereby restraining occurrence of failures such as mix-up of culture.

[2. Glove Box]

The glove box 110 will be described with reference to FIG. 3. FIG. 3 is the perspective view of the isolator system according to the embodiment 1.

As illustrated in FIG. 3, the glove box 110 is partitioned by the front plate 112 having the plurality of front openings 113, a bottom plate, a top plate, and left and right side plates. The glove box 110 includes, in the interior thereof: a work plate 111 on which work is conducted; and a divider 117. The box shaped work space A that is a space for conducting work is formed with the work plate 111, the divider 117, the top plate, and the left and right side plates. That is, the bottom of the work space A is configured with the work plate 111. The glove box 110 is a compartment that is formed with air tightness so as to restrain bacterial invasion from the exterior. Between the work plate 111 and the bottom plate, and between the back plate and the divider 117, a discharge path is formed which is for discharging gas in the work space A. In the glove box 110 according to the embodiment, the work plate 111, the divider 117, the bottom plate, the back plate, the top plate, and the left and right side plates are configured with stainless steel plates, which is easily cleaned and sterilized.

The front plate 112 includes the plurality of front openings 113, which are insertion portions for worker's hands. To each of the plurality of front openings 113, a glove (not shown) is mounted. front plate 112 is capable of opening/closing about a hinge provided an upper end thereof serving as an axis. Thus, the front surface of the glove box 110 can be opened/closed. Openings for mounting the pass box 170 and the incubator 200 are formed in left and right side plates. In the glove box 110, the pass box 170 is mounted to the opening in the right side plate, and the door of the opening of the pass box 170 configures a part of the right side plate. And, the incubator 200 is mounted to the left opening in the left side plate, and the door of the incubator 200 configures a part of the side plate. A worker conducts work in the interior of a work space A through gloves at the time of working. On the top plate, a pendant rod for hanging material used in operations is provided.

[3. Work Plate]

Figure 4:
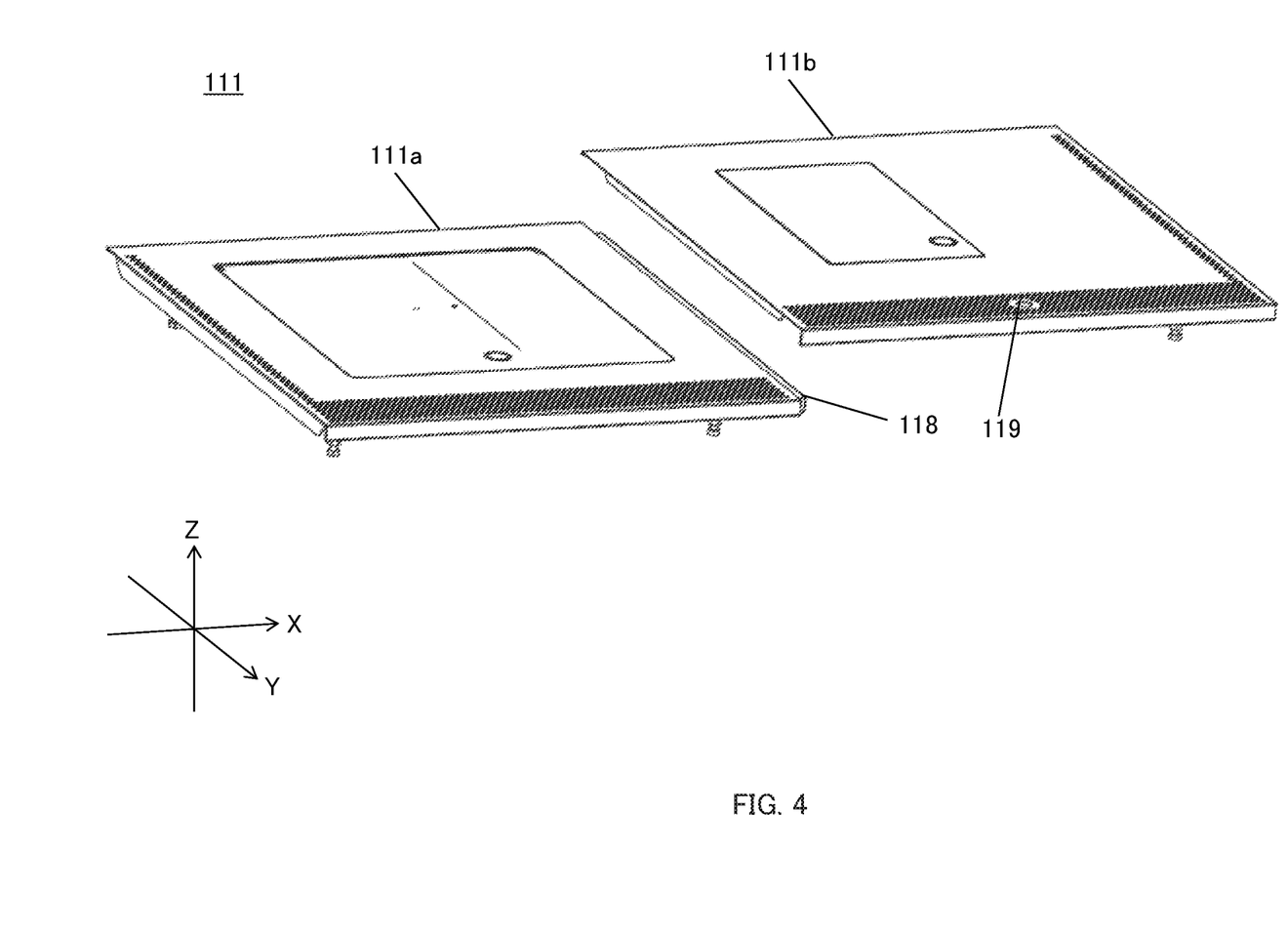
FIG. 4 is a perspective view of a work plate according to the embodiment 1 which is removed from a glove box.
Figure 5:
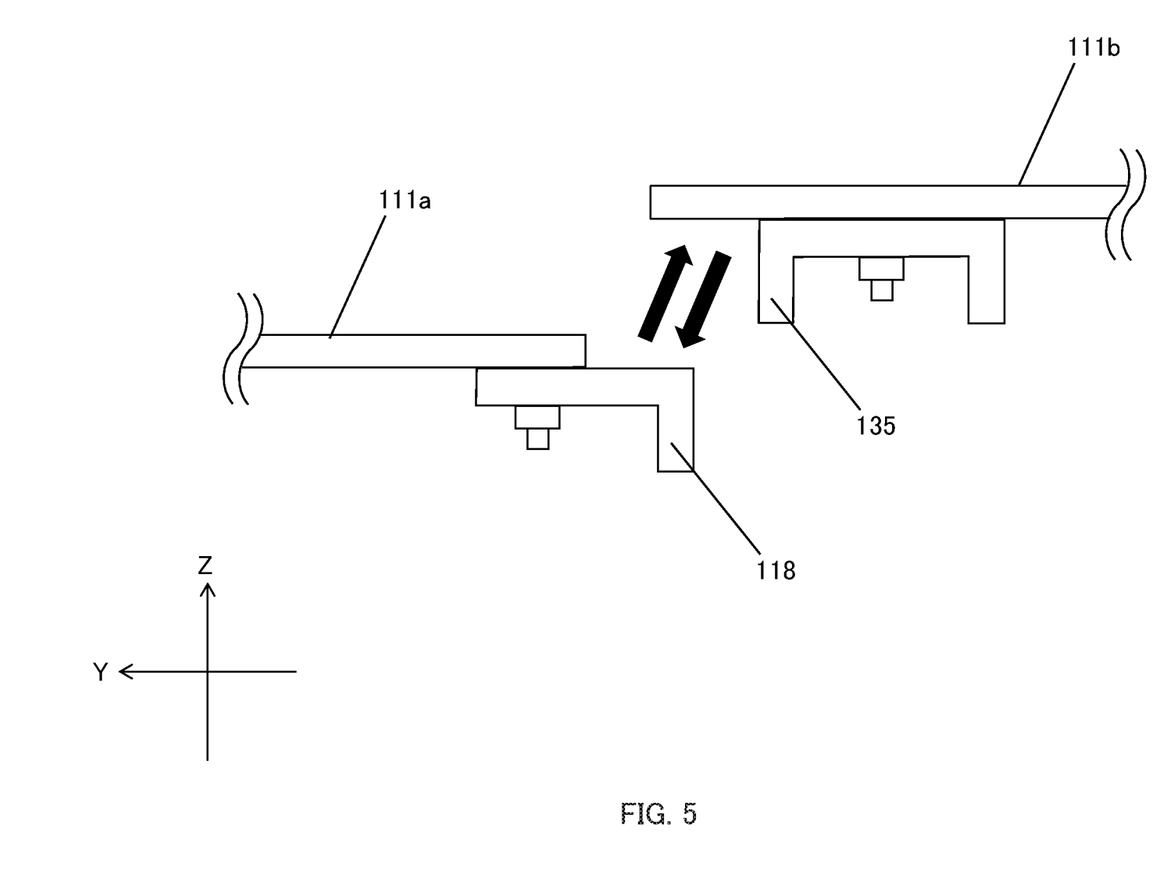
FIG. 5 is a cross sectional view in the vicinity of a receiving portion when the work plate according to the embodiment 1 is removed from the glove box.
Figure 6:
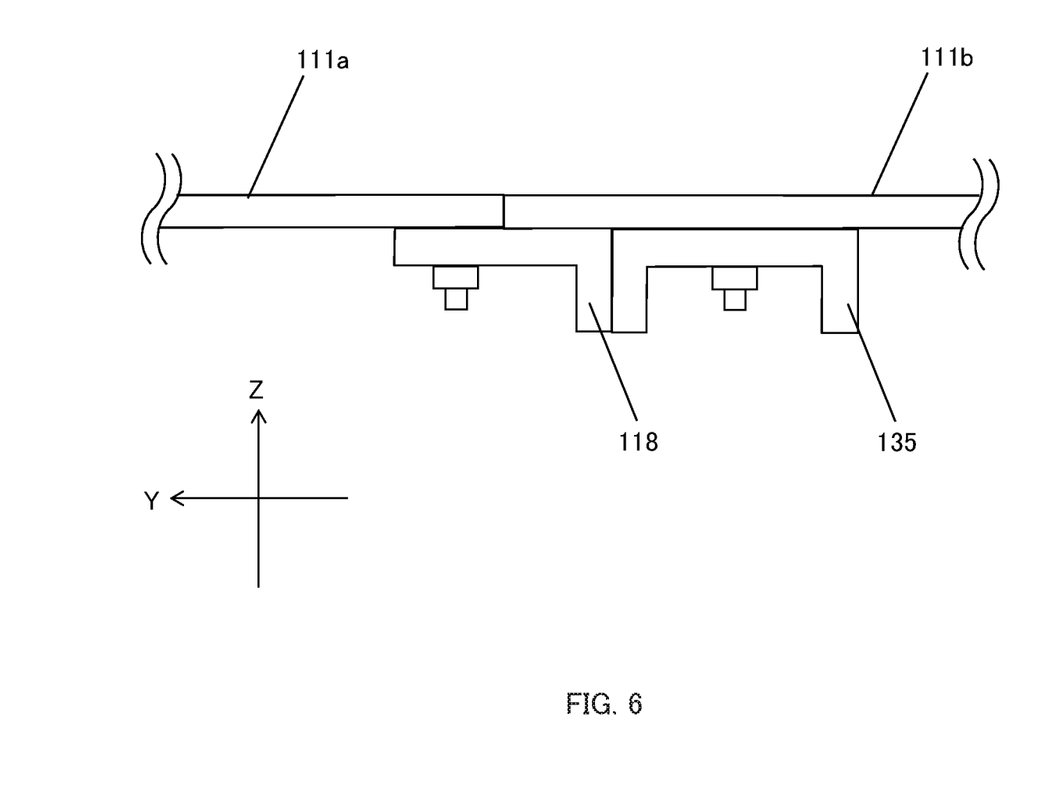
FIG. 6 is a cross sectional view in the vicinity of the receiving portion when the work plate according to the embodiment 1 is attached to the glove box.

The work plate 111 will be described with reference to FIGS. 4 to 8. FIG. 4 is a perspective view of a work plate 111 according to the embodiment 1 which is removed from a glove box 110. FIG. 5 is a cross sectional view of the same. FIG. 6 is a cross sectional view in the vicinity of a receiving portion when work plate according to the embodiment 1 is attached to the glove box.

As illustrated in FIG. 4, the work plate 111 is configured with a first work plate 111a and a second work plate 111b obtained by dividing the work plate into right and left parts. The work plate 111 has a plurality of outlets, through which gas in the work space A is discharged, formed in the front end portion and the left and right end portions. As illustrated in FIGS. 5 and 6, the side edge (right side edge) of the first work plate 111a for being in contact with the second work plate 111b, a receiving portion 118 which is located below the first work plate 111a is arranged extending towards the second work plate 111b (rightward in the figures). On the receiving portion 118, the side edge (left side edge) of the second work plate 111b for being in contact with the first work plate 111a is placed detachably. When the second work plate 111b is placed on the receiving portion 118 of the first work plate 111a, the top surfaces of the first work plate 111a and the second work plate 111b are disposed substantially in a same plane. The second work plate 111b has a hole 119 formed thereon, to which a worker hooks his/her finger to remove the second work plate 111b from the glove box 110 by pulling it up.

In the foregoing configuration, when removing the work plate 111 from the glove box 110, a worker first removes the second work plate 111b. The worker hooks his/her finger to the hole 119 of the second work plate 111b, and pulls up the second work plate 111b to remove the second work plate 111b. Then, the worker holds the first work plate 111a with grabbing the right side edge of the plate, the adjacent space of which is not occupied by the second work plate 111b, and pulls up the first work plate 111a to remove the first work plate 111a.

Figure 7:
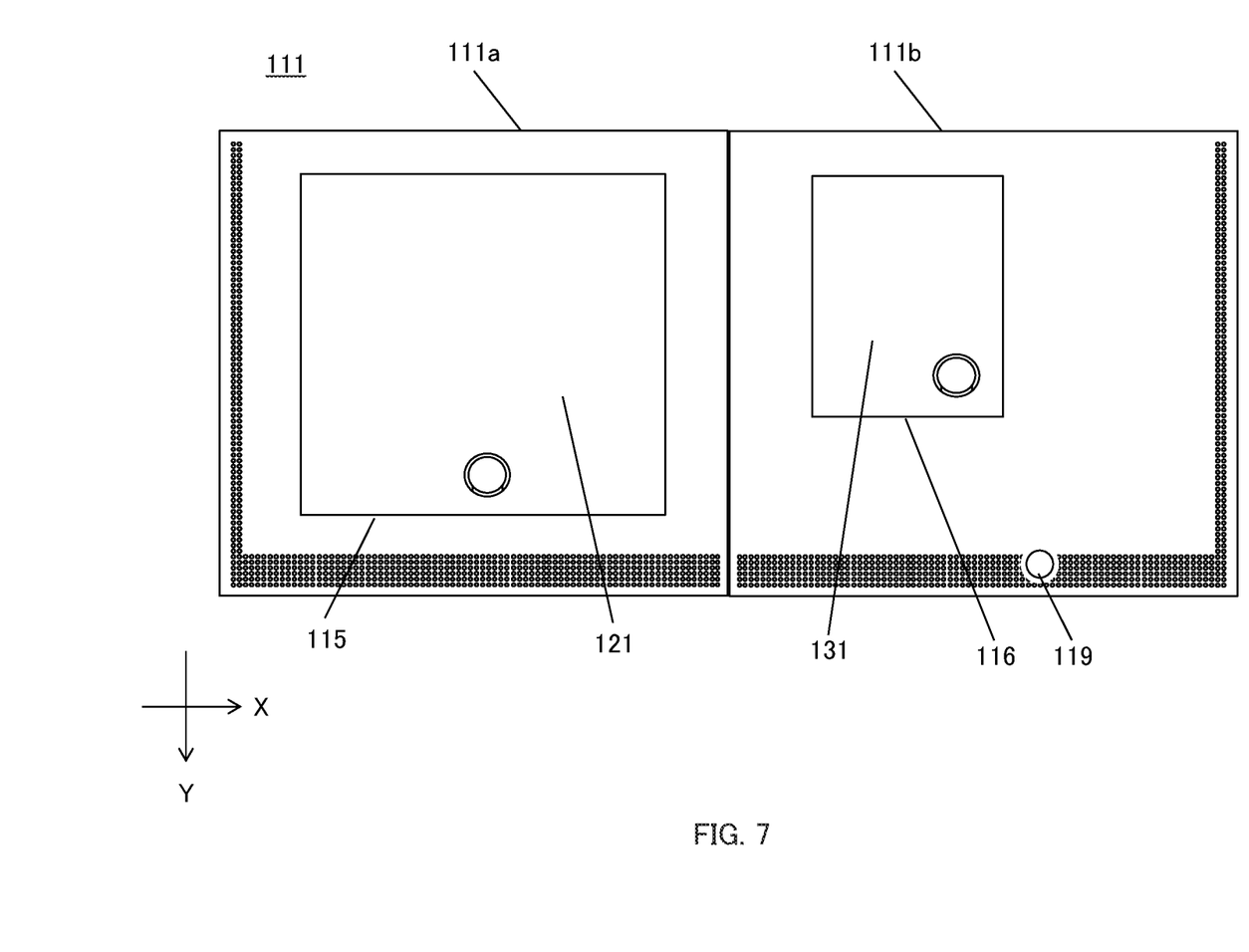
FIG. 7 is a top view of the work plate according to the embodiment 1 when it is attached to the glove box.

FIG. 7 is a top view of the work plate according to the embodiment 1 when it is attached to the glove box. As illustrated in FIG. 7, a connection opening 115 for connecting the centrifuge unit 120 (see FIG. 3), provided below the work plate 111, is formed in the first work plate 111a. A centrifuge cover 121, which configures a part of the first work plate 111a and is capable of opening/closing the connection opening 115, is mounted via hinges to the first work plate 111a. The centrifuge cover 121 is capable of opening/closing upwards by moving around the hinges. The centrifuge cover 121 has a hole formed thereon, to which a worker hooks his/her finger at the time of opening the centrifuge cover 121 by pulling it upwards. In addition, the centrifuge cover 121 includes an anti-drop cover via a spring hinge, the cover configuring a part of the first work plate 111a and being capable of opening/closing the hole.

A connection opening 116 for connecting the observation unit 130 (see FIG. 3), provided below the work plate 111, is formed in the second work plate 111b. An observation device cover 131, which configures a part of the second work plate 111b and capable of opening/closing the connection opening 116, is mounted via hinges to the second work plate 111b. The observation device cover 131 is capable of opening/closing upwards by moving around the hinges. The observation device cover 131 has a hole formed thereon, to which a worker hooks his/her finger at the time of opening the observation device cover 131 by pulling it upwards. In addition, the observation device cover 131 includes an anti-drop cover via a spring hinge, the cover configuring a part of the second work plate 111b and being capable of the hole.

In such a configuration, in the case of using the centrifuge unit 120, a worker hooks his/her finger to a hole from the work space A and open the centrifuge cover 121 upwards, to connect the work space A to the centrifuge unit 120. Similarly, in the case of using the observation unit 130, a worker hooks his/her finger to a hole from the work space A and open the observation device cover 131 upwards, to connect the work space A to the observation unit 130. Then, the observation device in the observation unit 130 moves upwards/downwards by lifting means.

Figure 8:
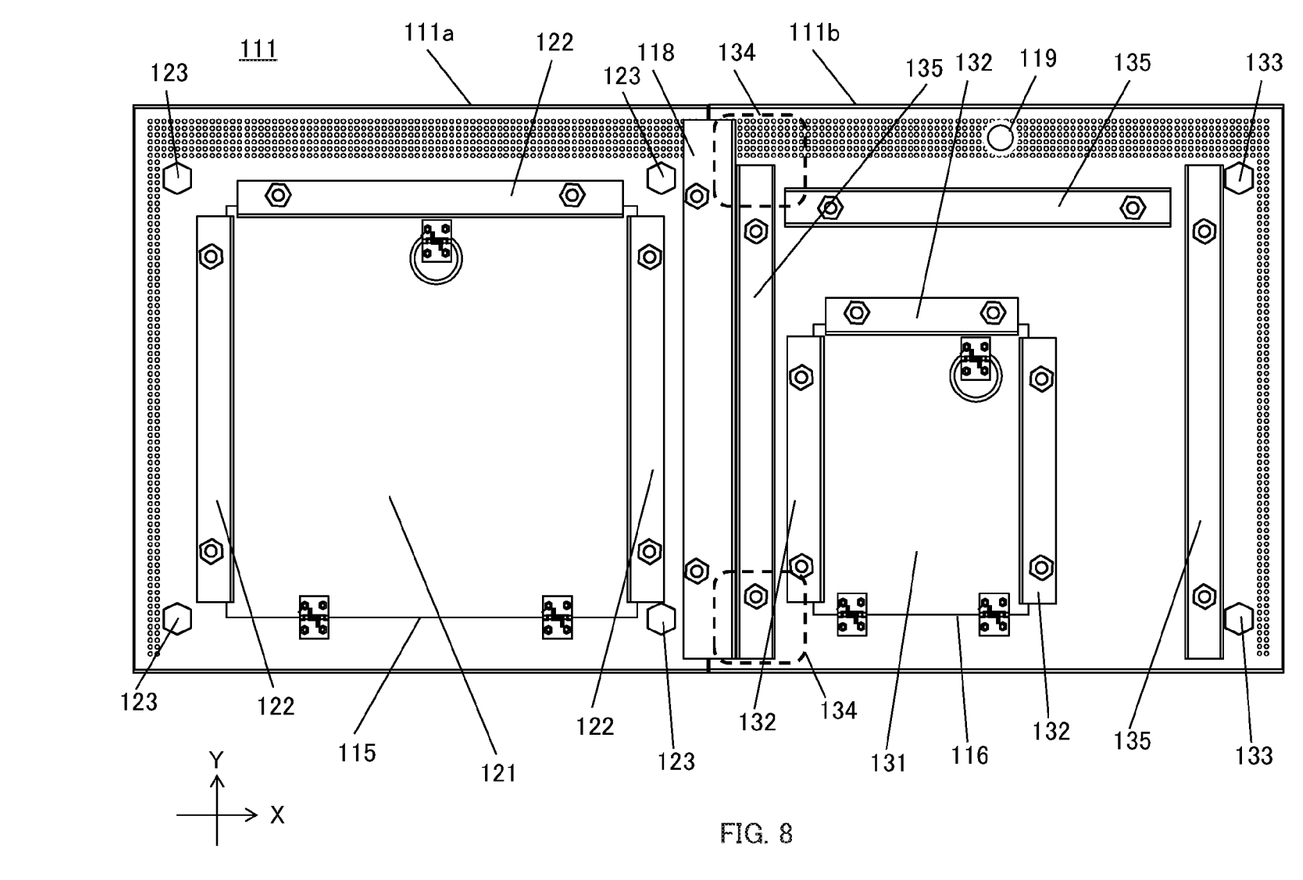
FIG. 8 is a bottom view of the work plate according to the embodiment 1 when it is attached to the glove box.

FIG. 8 is a bottom view of the work plate according to the embodiment 1 when it is attached to the glove box. As illustrated in FIG. 8, on the lower surface of the first work plate 111a, receiving portions 122 which support ends of the centrifuge cover 121 are disposed on the periphery of connection opening 115. When the centrifuge cover 121 is placed on the receiving portions 122, the top surface of the centrifuge cover 121 is disposed substantially in a same plane as the top surface of the first work plate 111a. First supporting legs 123 are provided on corner portions of the lower surface of the first work plate 111a.

On the lower surface of the second work plate 111b, receiving portions 132 which support ends of the observation device cover 131 are disposed on the periphery of the connection opening 116. When the observation device cover 131 is placed on the receiving portions 132, the top surface of the observation device cover 131 is disposed substantially in a same plane as the top surface of the second work plate 111b. In the second work plate 111b, second supporting legs 133 are provided on corner portions of the lower surface of the plate 111b, on the opposite side edge (right side edge) to the side edge (left side edge) which is in contact with the first work plate 111a. On the other hand, in the second work plate 111b, corner portions of the lower surface of the plate 111b on the side edge (left side edge) which is in contact with the first work plate 111a are portions 134 in which no second supporting leg 133 is formed. In the second work plate 111b, a reinforcing portion 135 which prevents the second work plate 111b from bending or vibrating are provided on the lower surface on the side edge (left side edge) which is in contact with the first work plate 111a. Additional reinforcing portions 135 are provided on the front side and the right side of the second work plate 111b.

[4. Effects, Etc.]

As mentioned above, in the present embodiment, the isolator system 100 includes: the box-shaped glove box 110 (body case) having, in the interior thereof, a work space A for operation in a sterile environment and also having, in a front surface thereof, the front opening 113 (insertion portion) for inserting a worker's arm; and an air-conditioning unit 150 (air-conditioning portion) configured to supply gas in the work space A of the glove box 110 or to discharge gas in the work space A. The bottom of the work space A is configured with the work plate 111. A discharge path which discharges gas in the work space A is formed below the work plate 111, and the work plate 111 is configured with the first and second work plates 111a and 111b obtained by dividing the work plate into right and left parts. On the side edge (right side edge) of the first work plate 111a for being in contact with the second work plate 111b, the receiving portion 118 which is located below the first work plate 111a is arranged extending towards the second work plate 111b (rightward). On the receiving portion 118, the side edge (left side edge) of the second work plate 111b for being in contact with the first work plate 111a is placed detachably.

Thus, in the isolator system 100, the work plate 111 is divided into right and left parts, and the second work plate 111b is supported by the first work plate 111a. This prevents vibration of the work plate 111. Thus, it is possible to provide an isolator system whose workability in worker's operations is improved. And, in the isolator system 100, when cleaning the discharge path located below the work plate 111, it becomes easier to attach/detach the first and second work plates 111a and 111b because the work plate 111 is divided into right and left parts. Thus, an isolator system can be achieved in which ease of cleaning and workability in worker's operations are improved.

Further, in the present embodiment, when the second work plate 111b is placed on the receiving portion 118 of the first work plate 111a, the top surfaces of the first and second work plates 111a and 111b are disposed substantially in a same plane.

Thus, the work plate 111 which is divided into right and left parts does not significantly deteriorate workability in worker's operations on the work plate 111.

Further, in the present embodiment, the first supporting legs 123 are provided on corner portions of the lower surface of the first work plate 111a. The second supporting legs 133 are provided on corner portions of the lower surface of the second work plate 111b on the opposite side edge (right side edge) to the side edge (left side edge) which is in contact with the first work plate 111a. And, corner portions of the lower surface of the second work plate 111b on the side edge (left side edge) which is in contact with the first work plate 111a are the portions 134 in which no second supporting leg 133 is formed.

Thus, since the weight of the second work plate 111b is supported by the receiving portion 118 of the first work plate 111a, the top surface of the first work plate 111a and the top surface of the second work plate 111b are more likely to be placed in a same plane. In addition, it is possible to prevent the vibration of the first and second work plates 111a and 111b. This can improve workability in worker's operations.

Further, in the present embodiment, the reinforcing portion 135 which prevents the second work plate 111b from bending or vibrating is provided in the lower surface of the second work plate 111b on the side edge (left side edge) which is in contact with the first work plate 111a.

Thus, it is possible to prevent the vibration of the first and second work plates 111a and 111b. This can improve workability in worker's operations.

Further, in the present embodiment, a centrifuge unit 120 (first device) used in operations is provided below the glove box 110. In the work plate 111, a connection opening 115 (first opening) for connecting work space A to the centrifuge unit 120 is provided, and the centrifuge cover 121 (first lid) which covers the connection opening 115 in a manner capable of opening/closing is also provided.

This enables a worker to perform necessary operations without taking an object out of the work space A. This can improve workability in worker's operations.

Further, in the present embodiment, the centrifuge unit 120 is provided below the first work plate 111a. The connection opening 115 and the centrifuge cover 121 are provided in the first work plate 111a.

Thus, when a worker cleans the discharge path below the first work plate 111b and picks up a thing which has been dropped in the discharge path, the worker can reach, without removing the first work plate 111b, by opening the centrifuge cover 121 and inserting his/her hand from the connection opening 115. In the isolator system 100, when removing the first work plate 111a, it is necessary to remove first the second work plate 111b because the first work plate 111a supports the second work plate 111b. But, in the isolator 100, the connection opening 115 and the centrifuge cover 121 are provided in the first work plate 111a. Thus, when a worker cleans only the discharge path located below the first work plate 111a, the worker can reach, without removing the second work plate 111b, below the first work plate 111a by opening the centrifuge cover 121 and inserting his/her hand from the connection opening 115.

Further, in the present embodiment, below the second work plate 111b, the observation unit 130 (second device) used in operations is provided. In the second work plate 111b, the connection opening 116 (second opening) for connecting the work space A to the observation unit 130 is provided, and also the observation device cover 131 (second lid) which covers the connection opening 116 in a manner capable of opening/closing is provided. The connection opening 115 has a larger opening area than that of the connection opening 116. That is, the connection opening 115 having a larger opening area is provided in the first work plate 111a which supports the second work plate 111b.

Thus, as mentioned above, when a worker wants to reach only the discharge path located below the first work plate 111a, the worker can reach, without removing the second work plate 111b, below the first work plate 111a by opening the centrifuge cover 121 and inserting his/her hand from the connection opening 115.

What is claimed is:

1. An isolator system comprising:
    a box-shaped body case having, in an interior thereof, a work space for operation in a sterile environment and also having, in a front surface thereof, an insertion portion into which a worker's arm is inserted; and
    an air-conditioning portion configured to supply gas in the work space of the body case or to discharge gas in the work space, wherein:
    a bottom of the work space is configured with a work plate,
    a discharge path configured to discharge gas in the work space is formed below the work plate,
    the work plate is configured with first and second work plates obtained by dividing the work plate into right and left parts,
    a receiving portion located below the first work plate and arranged to extend toward the second work plate,
    a side edged of the first work plate faces a side edge of the second work plate,
    the side edge of the first work plate being in contact with the second work plate, and
    on the receiving position, the side edge of the second work plate to be in contact with the first work plate is placed detachably.

2. The isolator system according to claim 1, wherein when the second work plate is placed on the receiving portion of the first work plate,
    a top surface of the first work plate and a top surface of the second work plate are disposed substantially in a same plane.

3. The isolator system according to claim 2, wherein:
    a first supporting leg is provided on a corner portion of a lower surface of the first work plate, a second supporting leg is provided on a corner portion of a lower surface of the second work plate, on an opposite side edge to a side edge which is in contact with the first work plate, and a corner portion of the lower surface of the second work plate on the side edge which is in contact with the first work plate is a portion in which no second supporting leg is formed.

4. The isolator system according to claim 3, wherein in the lower surface of the second work plate, a reinforcing portion configured to prevent the second work plate from bending or vibrating is provided on the side edge of the second work plate which is in contact with the first work plate.

5. The isolator system according to claim 2, wherein in a lower surface of the second work plate, a reinforcing portion configured to prevent the second work plate from bending or vibrating is provided on the side edge of the second work plate which is in contact with the first work plate.

6. The isolator system according to claim 2, wherein:

below the body case, a first device used in an operation is provided, and in the work plate, a first opening to reach the first device from the work space is provided, and a first lid which covers the first opening in a manner capable of opening/closing is provided.

7. The isolator system according to claim 6, wherein:

the first device is provided below the first work plate, and the first opening and the first lid are provided in the first work plate.

8. The isolator system according to claim 7, wherein:

below the second work plate, a second device used in an operation is provided, in the second work plate, a second opening to reach the second device from the work space is provided, and a second lid which covers the second opening in a manner capable of opening/closing is provided, and the first opening has a larger opening area than that of the second opening.

* * * * *